US00PP21668P3

(12) United States Plant Patent
Higaki

(10) Patent No.: US PP21,668 P3
(45) Date of Patent: Jan. 25, 2011

(54) *HYDRANGEA* PLANT NAMED 'MERRITT WHITE'

(50) Latin Name: *Hydrangea macrophylla (Thunb.)*
Varietal Denomination: Merritt White

(75) Inventor: Harrison Masami Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 12/322,241

(22) Filed: Jan. 30, 2009

(65) Prior Publication Data

US 2010/0199396 P1 Aug. 5, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent L Bell
(74) *Attorney, Agent, or Firm*—Charles R. Cypher; James R. Cypher

(57) ABSTRACT

A new and distinct cultivar of *Hydrangea macrophylla* (Thunb.) named 'Merritt White' was found in a field of the patented cultivar 'Ravel'—U.S. Plant Pat. No. 10,152. The cultivar 'Merritt White' has white sepals at maturity and is distinguished from other similar cultivars of which the inventor is aware by the unique manner in which the inflorescence ages. As the mature sepals age and turn green they are highly resistant to burning and turning brown. The new variety 'Merritt White' further possesses the favorable characteristics of a compact growth habit and long lasting large inflorescences.

5 Drawing Sheets

Latin name of the genus and species of the plant claimed: The new plant is a variety of *Hydrangea macrophylla* (Thunb.).

Variety denomination: The new plant has been given the varietal designation 'Merritt White'.

BACKGROUND OF THE INVENTION

This invention relates to a new and distinct cultivar of the *Saxifragaceae* family. The botanical name of the plant is *Hydrangea macrophylla* (Thunb.). The varietal denomination is 'Merritt White'.

The new cultivar was found in a cultivated area of the plant *Hydrangea macrophylla* (Thunb.) 'Ravel', which is the subject of U.S. Plant Pat. No. 10,152, granted Dec. 16, 1997. 'Ravel' is characterized by the pigmentation pattern of its sepals with the base of the sepals lacking pigmentation and the tips and blades developing more and more color as the inflorescence ages, creating a bi-color inflorescence.

The new cultivar 'Merritt White' has been successfully asexually reproduced through three successive generations under controlled environmental conditions at a nursery in Half Moon Bay, Calif. under the direction of the inventor with its distinguishing characteristics remaining stable.

'Merritt White' is characterized by its ability to withstand changes in light levels, making it ideal for commercial sale in pots. Its leaves do not easily turn chlorotic or brownish due to fluctuations in light levels. Potted plants for commercial sale are exposed to fluctuating light levels as they are transported and prepared for sale. The new variety is also characterized by the ability of its cuttings to establish roots and to root quickly. See table 1 below.

TABLE 1

Comparison with other cultivars.

| | 'Merritt White' (current variety) | 'Glory' (U.S. plant patent applied for) | 'White Robe' U.S. Plant Pat. No. 15,192 | 'Snowball' unpatented variety |
|---|---|---|---|---|
| Relative Height | Medium | Compact | Tall | Compact |
| Infloresence Uniformity | Good | Excellent | Acceptable | Poor |
| Relative resistance to browning of sepals when stressed by moderate drought | Acceptable | Excellent | Excellent | Very Poor |
| Relative flower longetivity | Acceptable | Excellent | Good | Poor |
| Crop time | Standard | Very early | Late | Early |
| Relative ease of branching when pinched | Good | Excellent | Acceptable | Excellent |

The new variety of *Hydrangea* as described herein is further characterized by its compact growth habit, and its large, long lasting inflorescences.

Asexual reproduction was first accomplished when vegetative cuttings were taken from the initially selected plant. Examination of asexually reproduced, successive generations grown in at Half Moon Bay, Calif. show that the combination of characteristics as herein disclosed for 'Merritt White' remains firmly fixed.

DESCRIPTION OF THE DRAWINGS

The accompanying drawings consist of color photographs that show the typical plant form, including the inflorescence, foliage, and sepals.

The plant shown is approximately 1 years old. The plant started out as a cutting, taken from the stem of a grown plant. Two leaves were attached to the stem cutting. The cutting was placed in a 6" pot with *hydrangea* soil that would produce blue pigmentation in *Hydrangeas* that have pigmentation in their sepals. The cutting was placed under mist for 3 to 4 weeks until the cutting rooted. The cutting was then moved out of the misting area, but left under glass. Once the cutting produced roots, the plant was fertilized approximately twice a week. The plant was kept inside under glass for 4 to 5 more weeks and then moved outside, and fertilized once a week.

DESCRIPTION OF THE NEW PLANT

Figure 1:
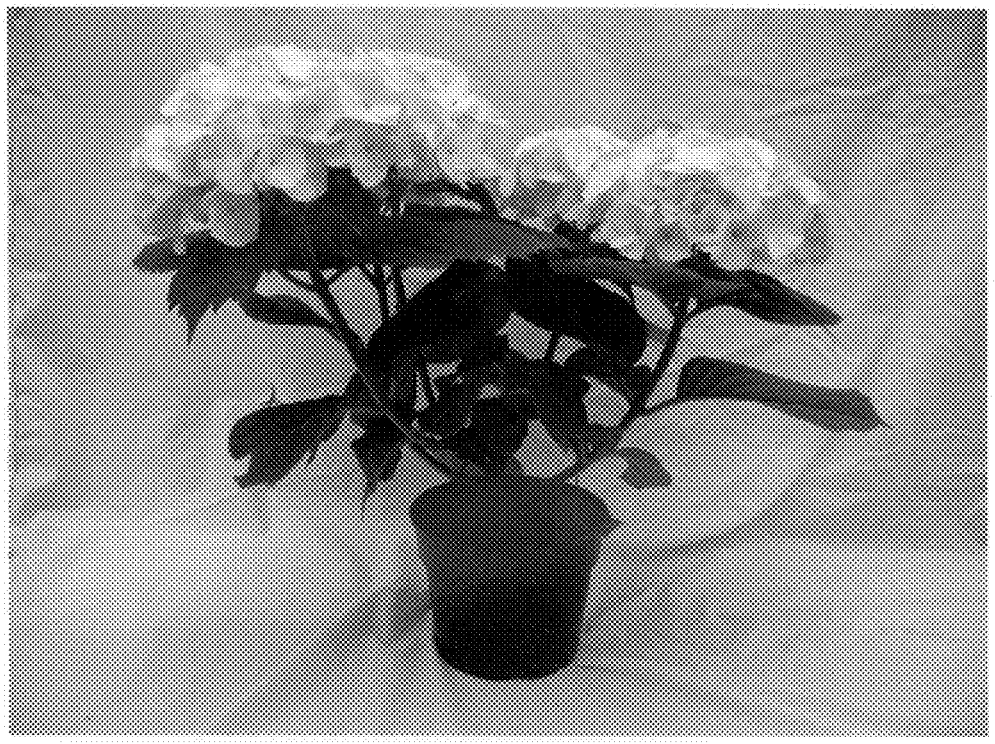
FIG. 1 is a view of an entire plant, grown in a 6" pot, showing its form, compact growth habit, dark green foliage, inflorescence, and white sepals.
Figure 2:
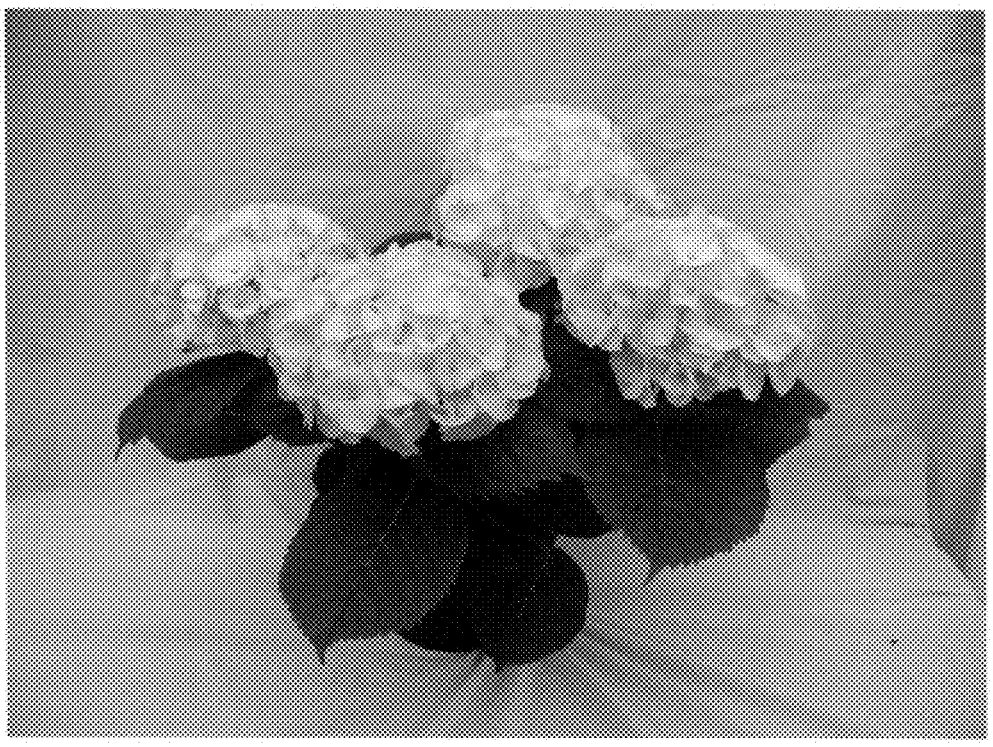
FIG. 2 is a view of the entire plant showing its form, compact growth habit, dark green foliage, inflorescence, and white sepals.
Figure 3:
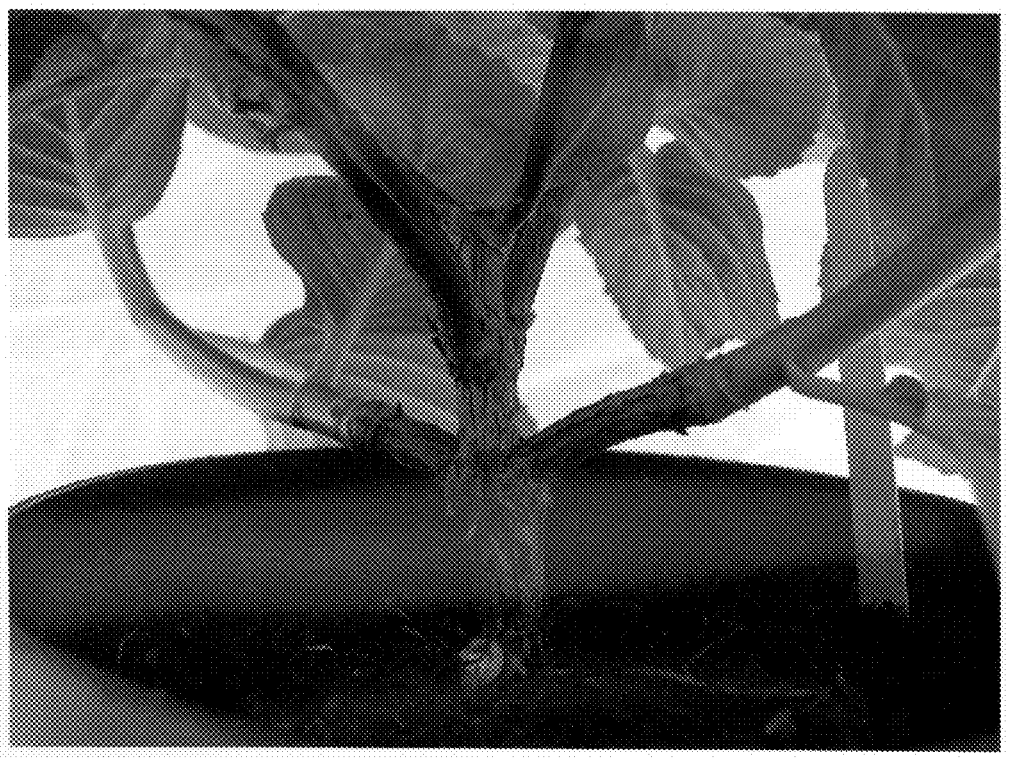
FIG. 3 is a view of the base of the plant of the new variety.
Figure 4:
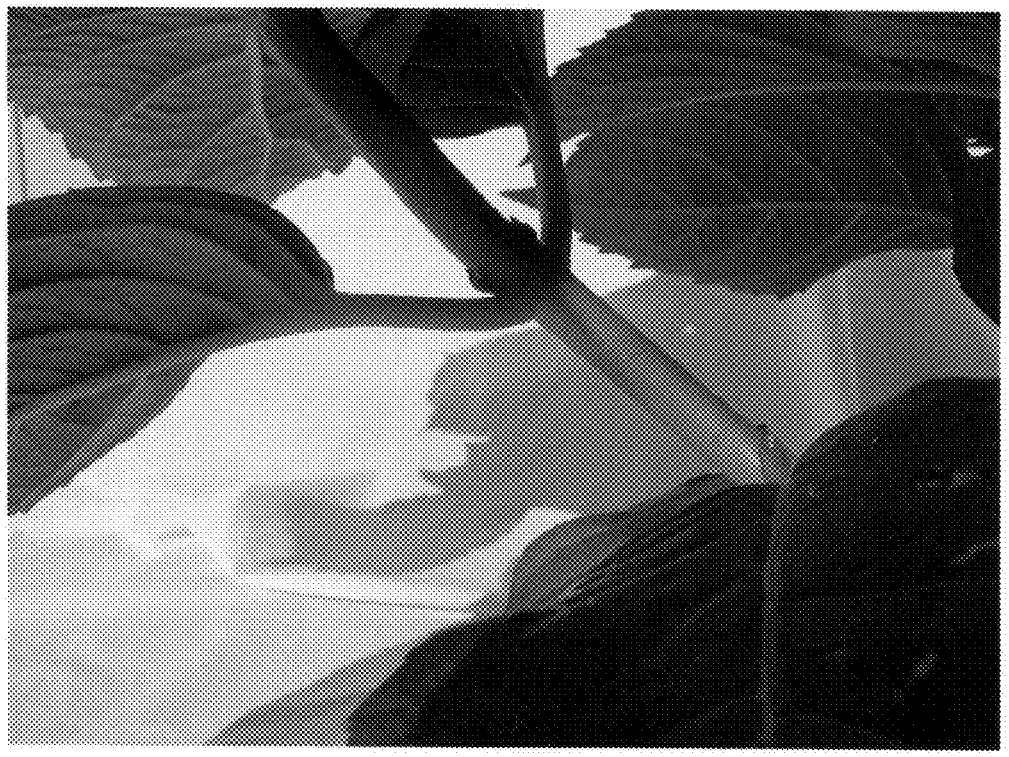
FIG. 4 is a close-up view of the stem of the plant of the new variety.
Figure 5:
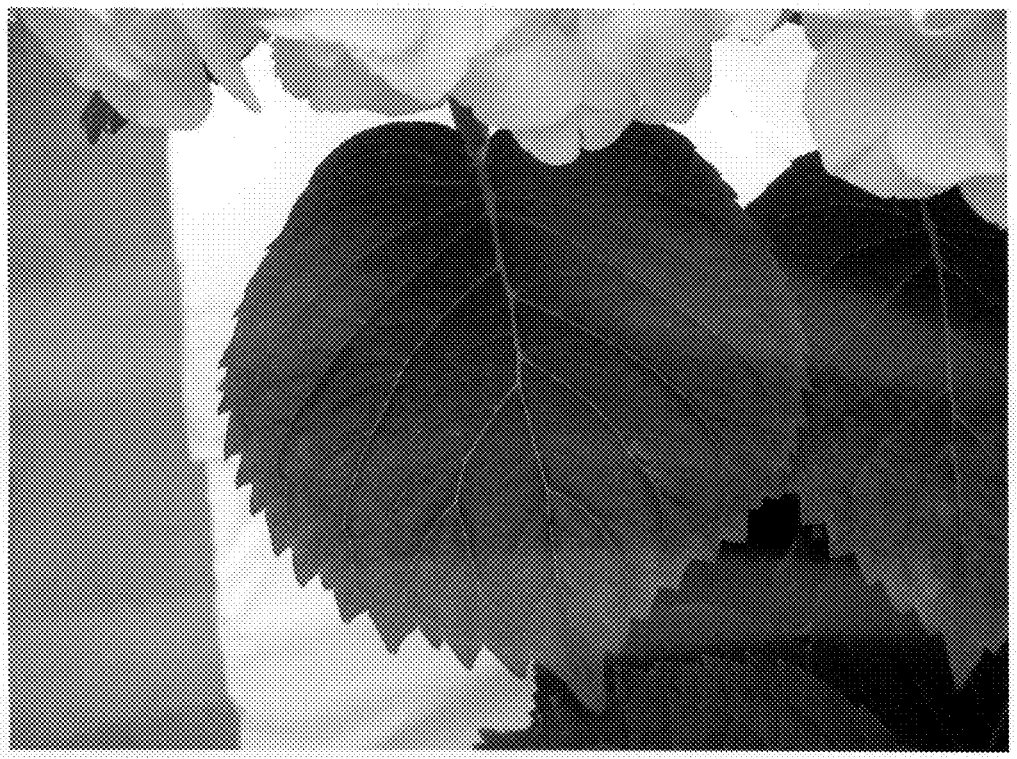
FIG. 5 is a close-up view of the upper side of a leaf of the plant of the new variety.
Figure 6:
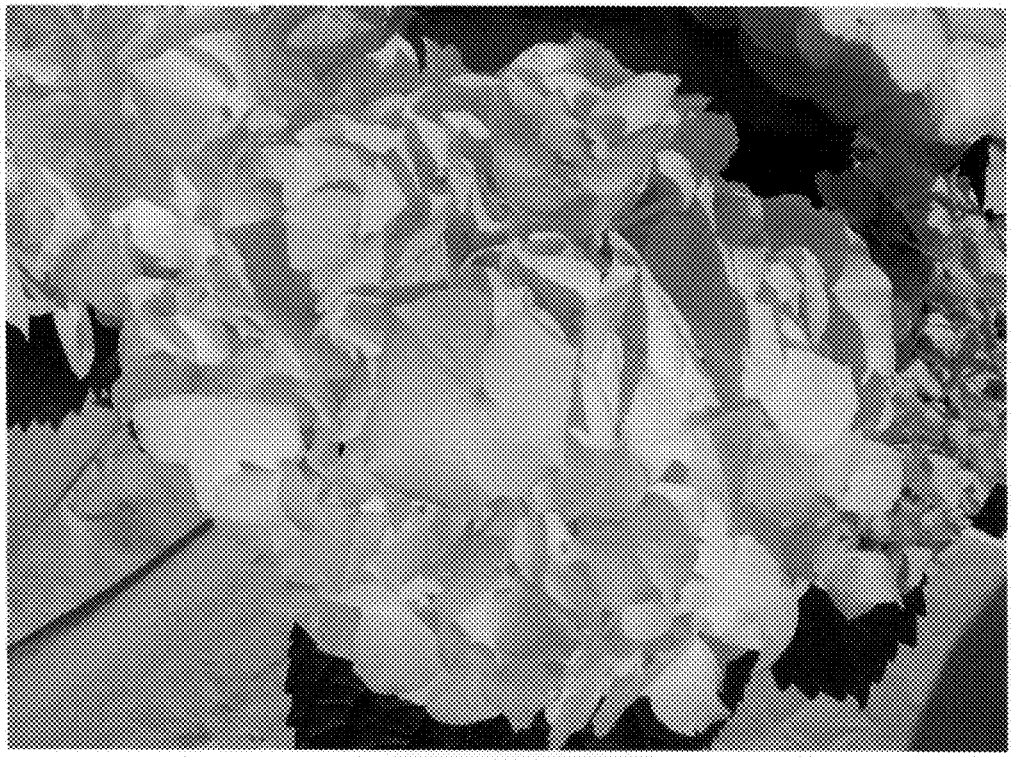
FIG. 6 is a close-up view taken from above of a mature inflorescence of the new cultivar showing its large inflorescence.
Figure 7:
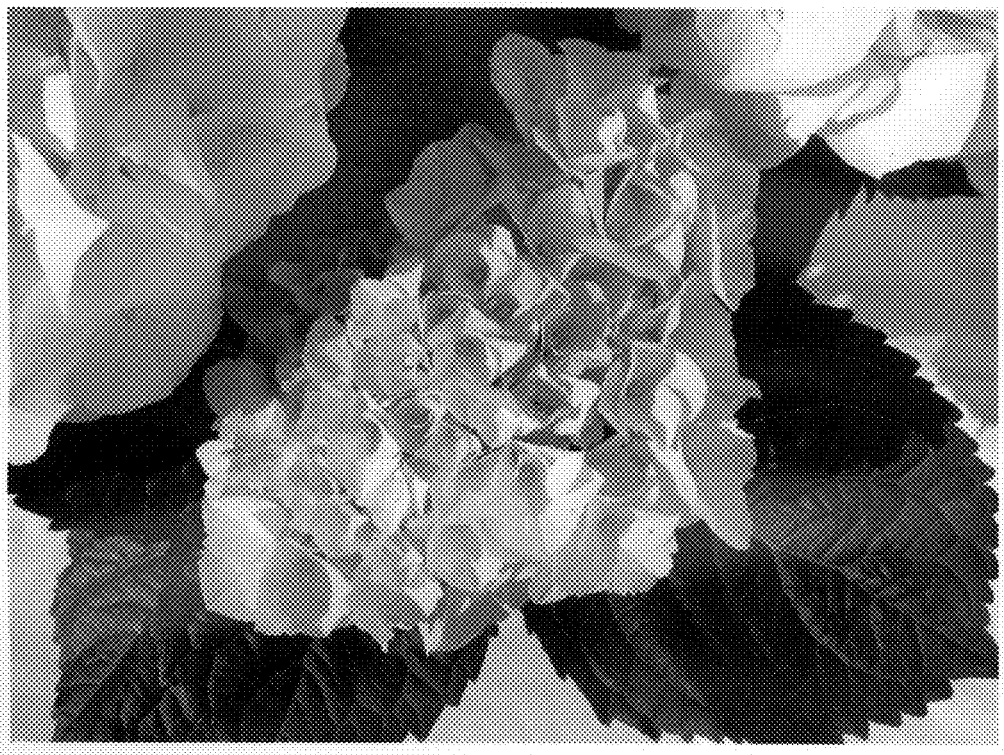
FIG. 7 is a close-up view taken from above of a relatively young inflorescence of the new cultivar.
Figure 8:
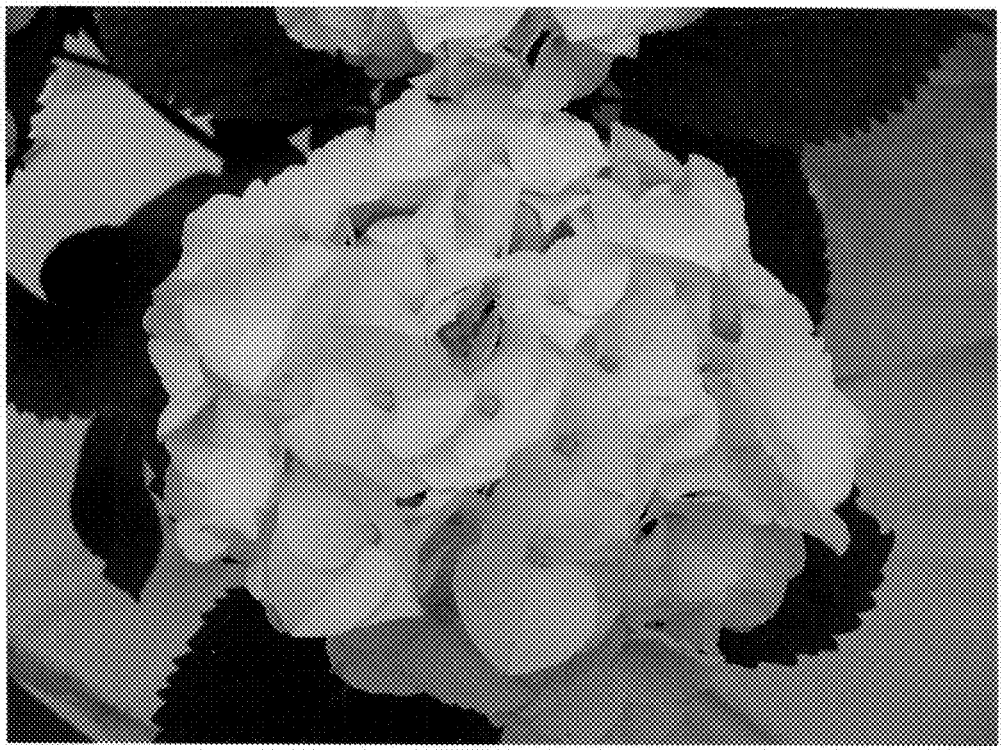
FIG. 8 is a close-up view taken from above of an inflorescence of the new cultivar that is more mature than the inflorescence of FIG. 7, but younger than the inflorescence of FIG. 6.
Figure 9:
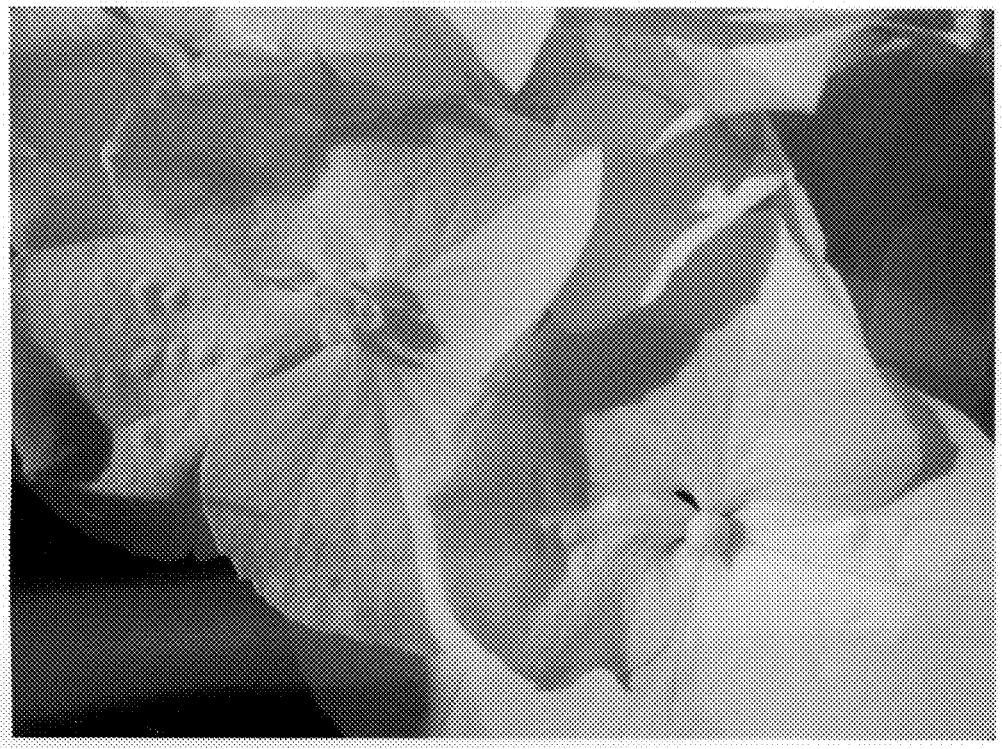
FIG. 9 is a close-up view of the individual florets illustrating the white sepals.
Figure 10:
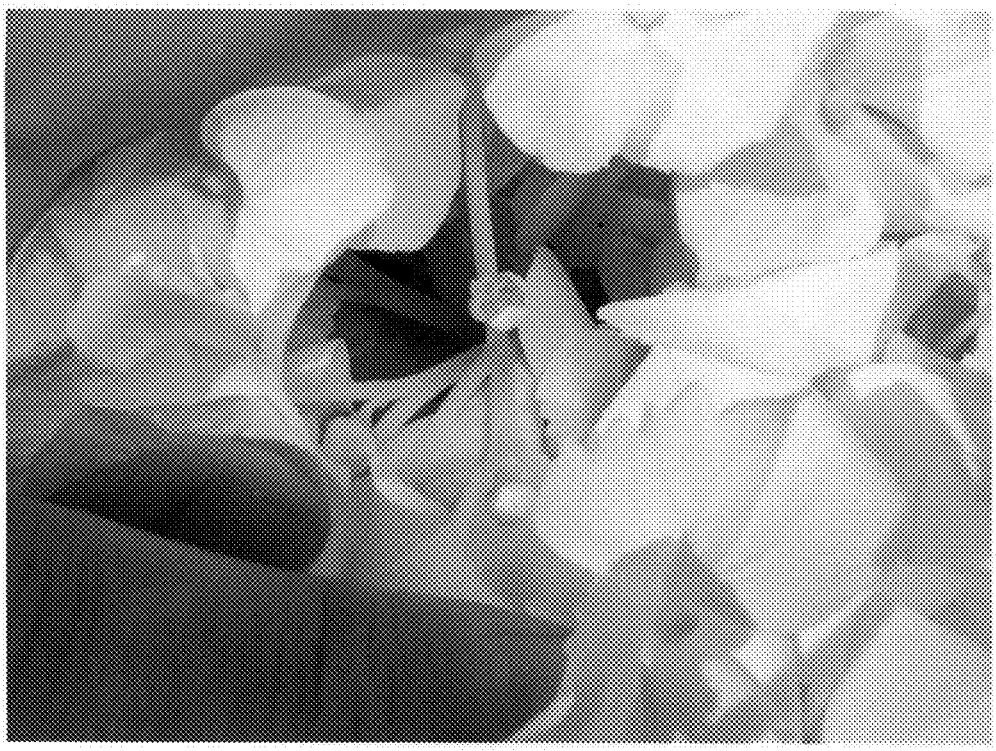
FIG. 10 is a close-up view of an individual non-sepalous floret which is otherwise hidden by the sepalous florets.

'Merritt White' has not been observed under all possible environmental conditions. The phenotype may vary significantly with variations in environment such as temperature, light intensity and day length. The following is a detailed description of a plant that started as a stem cutting and was grown in a 6" pot under the prevailing daylengths at Half Moon Bay, Calif. The plants observed were approximately 1 years old. The color determinations were made with The Royal Horticultural Society (R.H.S.) Colour Chart.

The plant:

*Origin.*—Sport.

*Parent.*—*Hydrangea macrophylla* (Thunb.) 'Ravel' which is the subject of U.S. Plant Pat. No. 10,152, granted Dec. 16, 1997.

*Classification.*—Botanic. — *Hydrangea macrophylla* (Thunb.) 'Merritt White'. Commercial. — Florist *Hydrangea* 'Merritt White'.

*Form.*—Upright, compact shrub. A typical plant with a mature infloresence that is ready for sale is approximately 38 cm high and has a diameter of 50 cm when grown in a 6" pot with appropriate soil amendments.

*Growth.*—Upright, vigorous growth habit. Inflorescence is large. The plant braches easily with shoots forming at the base of the plant. Lateral branches are similar in appearance and form to the main stems.

*Stems.*—Lenticels are present; stems become woody as they age. The color of typical young stems and young lateral branches is R.H.S. 145 A (green group). Woody stems and lateral branches are R.H.S. 199 A (grey-brown group) Typical internode length on mature stems and branches is approximately 1.75" to 2.5". Stems and lateral branches are approximately 5 to 7 mm in width. Stems and branches are smooth. Plant produces as many as 6 lateral branches when main stem in pinched above the third node.

*Foliage.*—Abundant. Leaves are opposite on stem and lateral branches. The blades of small mature leaves are approximately 14 cm long and 10 cm wide, while large mature leaves have blades that are as long as 18 cm long and as wide as 15 cm. Petioles can be as long as 2.5 cm and are typically 4 mm wide. The petioles are R.H.S. 145 C (yellow-green group). There can be as many as 5 leaf pairs on a new stem below the infloresence. Shape of leaf. — Elliptic with an acute apex and cordate base; margins are serrate. Texture. — Glabrous; veins dominate on the underside of the leaf and are sunken on the leaf surface. Color. — Mature leaves have an upper side that is R.H.S. 139 A (green group); under side is R.H.S. 147 C (yellow-green group). The veins of mature leaves are R.H.S. 145 C (yellow-green group) whether viewed from the top or the bottom of the leaf. Leaves are pinnately veined. The mid vein and veins branching off the midvein are large and prominent on the underside of the leaves.

Buds:

*Form.*—Globose; with 4 to 5 connate, elliptic, smooth petals. Buds in the very center of the inflorescence are non-sepalous. The majority of buds have sepals. They are approximately 1 mm by 1 mm. Very young floret buds are R.H.S. 145C (yellow-green group).

*Aspect.*—Smooth.

*Arrangement.*—Borne on branched panicles.

*Color.*—Buds and their petals and sepals are R.H.S. 145 C (yellow-green group), and whiten as the bud matures. Petals eventually fall off with reproductive organs.

Inflorescence:

*Form.*—Paniculate. Terminal. 100 or more individual flowers (florets) per inflorescence. Both sepalous florets and non-sepalous florets borne on same panicle with the sepalous florets hiding the non-sepaolous florets, when the inflorescence reaches maturity. An infloresence with 100 florets may have as many as 85 sepalous florets and 15 non-sepalous florets. Flowers do not produce a fragrance. The peduncle or panicle for the inforescence is strong and upright, and typically starts branching 1" above the last main leaf pair on the stem. Small leaves appear on pedicels low on the panicle. Color of the peduncle is R.H.S. 145 A (green group). Pedicels for the individual florets are predominately white (R.H.S. 155D (white group)) at maturity. Pedicels are typically 2 cm to 5 cm long, branch at many different angles and are approximately 2 mm in diameter.

*Size of inflorescence.*—Large. Individual inflorescence size is dependent on the number of florets. Typical infloresences can grow as large as 25 cm in diameter, and 15 cm high above the last full leaf pair.

*Shape.*—Clusters of numerous small florets; sepalous florets are flat and overlapping one another. Sepals are persistent. Sepals elongate and greens as the inflorescence ages past maturity. Non-sepalous florets are inconspicuous and hidden by sepalous florets.

*Appearance.*—Showy.

Florets:

*General.*—Sepalous florets are perfect and complete.

*Corrola.*—Generally there are 4 petals, and if there are 5 petals, they are all similarly sized.

*Reproductive organs.*—Stamens. — 8 to 10 stamens, with most florets having 8 stamens. Pollen is white — R.H.S. 155D (white group). Filament is approximately 2 mm long, and color depends on pH of the soil. Anther is 1 mm long. Anther is regular and basally attached. Stigma. — Two to three-pronged stigma on one pistil per floret. Stigma barely protrudes from the ovary. Ovary. — Green in color — R.H.S. 145 A (yellow-green group); single ovary that is partially inferior.

*Sepalous florets.*—Number of sepals. — 4 or 5 sepals per floret, usually 4. Aspect of sepals. — Smooth. Shape of sepals. — Reniform with acuminate apex, entire edges with some crenation. Edges often wavy when the floret is young. Size of sepals. — Usually 1 dominant sepal, 2 smaller but equally-sized sepals, and 1 small sepal. Largest sepal, when sepals are their whitest is typically 3 cm long and 4 cm wide, the medium sized sepals are typically 2.6 cm long by 2.8 cm wide, and the smallest sepals are typically 2.5 cm long and 2.6 cm wide. Coloration of sepals. — Predominately white (R.H.S. 155D (white group)) at maturity on both the upper surface and the lower surface.

I claim:

1. A new and distinct *Hydrangea macrophylla* plant named 'Merritt White' substantially as herein shown and described.

* * * * *